(12) United States Patent
Conroy (10) Patent No.: US 9,771,276 B2
(45) Date of Patent: Sep. 26, 2017

(54) WASTE STREAM EVALUATION AND SCREEN SELECTION SYSTEM

(71) Applicant: Jay R. Conroy, Dunedin, FL (US)

(72) Inventor: Jay R. Conroy, Dunedin, FL (US)

( * ) Notice: Subject to any disclaimer, the term of this patent is extended or adjusted under 35 U.S.C. 154(b) by 76 days.

(21) Appl. No.: 14/728,066

(22) Filed: Jun. 2, 2015

(65) Prior Publication Data
US 2015/0346073 A1  Dec. 3, 2015

Related U.S. Application Data

(60) Provisional application No. 62/006,286, filed on Jun. 2, 2014.

(51) Int. Cl.
G01N 15/06 (2006.01)
C02F 1/00 (2006.01)

(52) U.S. Cl.
CPC ......... *C02F 1/008* (2013.01); *G01N 15/0606* (2013.01); *C02F 2303/24* (2013.01)

(58) Field of Classification Search
CPC .. G01N 15/0606; C02F 1/008; C02F 2303/24
See application file for complete search history.

(56) References Cited

U.S. PATENT DOCUMENTS

| | | | |
|---|---|---|---|
| 7,416,668 B1 * | 8/2008 | Theodore | C02F 3/302 210/173 |
| 7,455,773 B1 * | 11/2008 | Harmon | C02F 9/00 210/603 |
| 8,808,537 B1 * | 8/2014 | Livingston | C02F 9/005 210/196 |
| 2004/0108270 A1 * | 6/2004 | Mueller | B01D 61/00 210/650 |
| 2005/0006305 A1 * | 1/2005 | Juby | C02F 3/2846 210/603 |
| 2006/0008865 A1 * | 1/2006 | Cote | B01D 35/027 435/34 |
| 2007/0215539 A1 * | 9/2007 | Conroy | B01D 33/333 210/400 |
| 2008/0296228 A1 * | 12/2008 | Sauvignet | B01D 21/0012 210/665 |
| 2009/0045120 A1 * | 2/2009 | Harmon | C02F 9/00 210/202 |
| 2009/0314722 A1 * | 12/2009 | Kelly | B01D 33/04 210/744 |
| 2012/0255902 A1 * | 10/2012 | Livingston | B01D 61/145 210/607 |
| 2014/0083936 A1 * | 3/2014 | Murthy | C02F 3/006 210/605 |
| 2014/0138329 A1 * | 5/2014 | Przekop | C02F 1/004 210/808 |
| 2015/0211976 A1 * | 7/2015 | David | B29C 67/0085 134/104.4 |

* cited by examiner

*Primary Examiner* — David Bolduc
(74) *Attorney, Agent, or Firm* — Johnson & Martin, PA; James David Johnson (57) ABSTRACT

A system and method for evaluating a flow pattern and downstream process for proper selection of screen type, opening and size for optimal screenings capture, operation time and capital outlay. The end result is a properly designed system that effectively protects downstream equipment and may save the customer money throughout the entire plant.

4 Claims, 13 Drawing Sheets

| Table 1: Test Itinerary at Saratoga County Sewer District No. 1 Wastewater Treatment Plant ||||
|---|---|---|---|---|
| Test # | Location Screen | Location in Channel | First Sieve | Second Sieve |
| 1 | Influent | Middle | 6mm UHMW Perf | None |
| 2 | Influent | Middle | 6mm Slotted | None |
| 3 | Influent | Middle | 2mm Metal Perf | None |
| 4 | Influent | Middle | 6mm UHMW Perf | 2mm Metal Perf |
| 5 | Influent | Middle | 6mm UHMW Perf | 4mm Metal Perf |
| 6 | Influent | Middle | 6mm Slotted | 2mm Metal Perf |
| 7 | Influent | Bottom | 6mm UHMW Perf | None |
| 8 | Influent | Bottom | 6mm Slotted | None |
| 9 | Effluent | Middle | 6mm UHMW Perf | None |
| 10 | Effluent | Middle | 6mm Slotted | None |
| 11 | Effluent | Middle | 2mm Metal Perf | None |
| 12 | Effluent | Middle | 6mm UHMW Perf | 2mm Metal Perf |
| 13 | Effluent | Middle | 6mm UHMW Perf | 4mm Metal Perf |
| 14 | Effluent | Middle | 6mm Slotted | 2mm Metal Perf |

WASTE STREAM EVALUATION AND SCREEN SELECTION SYSTEM

CROSS-REFERENCE TO RELATED APPLICATIONS

This application is a nonprovisional application of and claims priority from U.S. provisional patent application Ser. No. 62/006,286 filed on Jun. 2, 2014. The foregoing application is incorporated in its entirety herein by reference.

FIELD OF THE INVENTION

The invention is related to systems and methods for evaluating water and waste streams. More particularly, the invention is related to systems and methods for evaluating waste streams to select or size a screen.

BACKGROUND

The wastewater industry has responded to increasingly stringent plant effluent requirements with enhanced plant design and innovative technology. While these new procedures are able to treat higher volume flows for less money, these procedures require significant attention to each stage of the improved processes. It is generally accepted that unique plant designs have established and defined performance requirements in order to meet effluent regulations, but increasing emphasis on influent flow analysis is needed to optimize treatment.

Engineers, operators, and maintenance personnel alike have long since realized there are benefits in removing inorganic and settleable solids as early in the treatment process as possible, but preliminary treatment equipment has conventionally been selected more on requirements of downstream processes than influent characteristics. Specifically, as these processes increase in sophistication and sensitivity, plant design is driven towards finer upstream screening protection without further investigation into the type of solids presented to the plant. Generally, this can result in higher capital outlays, larger headworks structures, and frequently increases disposal of the organic and fecal material the plant is designed to treat.

Just as each plant has its own characteristics that dictate the amount of screening protection it requires, every collection system and the waste flow it receives are unique as well. The design of a collection system, constituents feeding the plant, stormwater infiltration, and variations in flow all have a direct impact on the quantity, size, and consistency of screenings in the influent flow of any given treatment plant. The Water Environment Federation (WEF), in co-operation with American Society of Civil Engineers (ASCE), did a study of the screenings volume relative to flow collected at 39 U.S. wastewater treatment plants. Their results proved that plant screenings are so unique they differ by a factor of 70 times. Even conservative sizing used by most screen manufacturers cannot properly account for fluctuations in screenings of this magnitude when calculations are based on peak flow and opening size alone.

What is needed is a method and system for testing with specialized equipment, which may analyze the solids loading characteristics of an individual plant to be expanded from generalized total suspended solids ("TSS") or biochemical oxygen demand ("BOD") ranges to stratification of solid sizes present in the waste stream. What is needed is a method and system for analysis of this data that help identify proper screen openings and capture ratios required by downstream processes while determining the appropriate screen type, size, and operational sequence determined by the unique inputs to the individual plant.

SUMMARY

The present invention advantageously provides a method and system for testing with specialized equipment, which may analyze the solids loading characteristics of an individual plant to be expanded from generalized TSS or BOD ranges to stratification of solid sizes presented in the waste stream. Additionally, the present invention advantageously provides a method and system for analysis of this data that help identify proper screen openings and capture ratios required by downstream processes while determining the appropriate screen type, size and operational sequence determined by the unique inputs to the individual plant.

Having more detailed information about the contents of the waste flow in these applications is critical in properly determining the correct screen type, grid, and size for the application. Some factors affecting fluctuations in the quantity, size, and consistency of screenings in the wastewater entering a municipal wastewater treatment plant are detailed below. The present invention advantageously facilitates collection of the information.

The system of the present invention analyzes multiple characteristics of the waste stream and collected data is evaluated for proper selection of screen type, opening, and size for optimal screenings capture, operation time, and capital outlay. The end result is a properly designed system that effectively protects downstream equipment and saves the customer money throughout the entire plant. The system and methods of the present invention advantageously maximize screening capture, measure existing screen performance, reduced chance of screen failure or headwork flooding, greatly improved hydraulic performance predictions, and quantifies loading in municipal wastewater, pulp and paper, food processing, brewery, pharmaceutical, and other unique waste streams.

The present invention may collect data to be evaluated to give a representation of solids loading at a testing site. The results may be compared with other facilities to determine valuable information for selecting and properly sizing screening equipment. Dual stage screens may be designed for balanced binding, headlosses, and screen size.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides a system for water and waste stream evaluation and screen selection and/or sizing. The system may include a collection system, which may evaluate an area of collection system and length of sewer line, number and size of pump stations, pump type and presence of coarse screenings or grinding at stations, equalization or storage basins, and septage and grease hauler dumping.

Additionally, a method is provided for evaluating a waste stream and selecting a screen relating to the same.

The system and methods may consider population factors, including density, hotels, resorts, laundry facilities, hospitals, sports stadiums, correctional and/or institutional facilities, and local industry. Headworks design may be considered for the evaluation, including length and slope of influent channel, number of channels and flow distribution, and/or pretreatment such as coarse screening or grit removal. Additionally, flow variations may be evaluated, including infiltration and intrusion, weather conditions like drought or heavy precipitation, and water use restrictions.

Just as each plant has its own characteristics that dictate the amount of screening protection it requires, every collection system and the waste flow it receives are unique as well. The design of a collection system, constituents feeding the plant, stormwater infiltration, and variations in flow all have a direct impact on the quantity, size, and consistency of screenings in the influent flow of any given treatment plant. WEF, in co-operation with ASCE, did a study of the screenings volume relative to flow collected at 39 U.S. wastewater treatment plants. Their results proved that plant screenings are so unique they differ by a factor of 70 times. Even conservative sizing used by most screen manufacturers cannot properly account for fluctuations in screenings of this magnitude when calculations are based on peak flow and opening size alone.

Having more detailed information about the contents of the waste flow in these applications is helpful in properly determining the correct screen type, grid, and size for the application. Some factors affecting fluctuations in the quantity, size, and consistency of screenings in the wastewater entering a municipal wastewater treatment plant are detailed below.

Illustrative benefits of flow analysis will now be discussed without limitation. Thorough analysis of flow to a treatment may provide an excellent return on investment. With focus on preliminary treatment, and screens in particular, the benefits extend from initial operation through the life cycle of the equipment selected.

The advantages of understanding the characteristics of solids in the waste stream begin with proper screen sizing to balance capital expense with long-term operation. To handle peak flows, a screen may be large enough to present enough open area to maintain appropriate water levels in the channel and velocities through the equipment. As solids blind the available open area, the screen may operate at sufficient speed and frequency to clean or present a new clean filtration area. The life of a screen's wear parts is determined by the speed and frequency in which the equipment is operated, therefore a larger screen operated slower and less frequently will outlast a smaller screen operated faster and more often. Flow analysis is an essential tool in determining the appropriate size screen to balance initial capital outlay and long-term screen operating costs.

Proper screen selection, sizing, and operation directly impact all downstream processes. If a screen is not protecting subsequent equipment as intended, maintenance costs can increase substantially while the life of that equipment can be reduced dramatically. Improper screening can also remove more organic material than desired. This can starve biological plant processes of the nutrients they were designed to treat while concurrently creating a screening disposal problem.

Visual inspection during flow analysis also provides useful information for design of screening handling and forecasting potential issues. Effective screening removes organic (fecal) and inorganic solids alike above a certain size. The higher amount of organic material the greater the plant's need for screenings handling, washing, and compaction. Examination of collected solids previews what the screens will collect and allows for proper screening handling design to separate inorganic and undesirable organic material for disposal while returning the biological content to the plant for treatment. An example of an undesirable organic material is a cotton rag. Identification of unexpected amounts of fibrous material, rags, grit, fats, oils, grease, and other large solids also aids in the screen type and opening selection. This may prevent potential surprises and poor screening performance.

Screening equipment will now be discussed. The screening equipment may include coarse and fine mechanical screening. Coarse screens are designed for removal of large solids and are meant for protection of pumps and collection systems. In municipal wastewater, they are often used in pump stations and CSO applications. While some treatment plants only operate with coarse screening, they are typically followed by finer screens further down the process. Normally coarse screens do not require screening, washing, or compaction as they primarily remove inorganic material and fecal washing is not necessary.

Fine screens are designed for medium to small solid size removal. In municipal wastewater systems, they are frequently incorporated into the preliminary treatment process at the headworks of a plant prior to grit removal. They are also used in pump stations, after grit removal and as a clarifier polishing when finer filtration is needed for protection of downstream processes. Because of the smaller openings, these screens remove larger amounts of fecal and organic material and are typically installed with screening handling equipment for washing and compaction of screenings prior to disposal.

Historically, mechanical coarse screens have openings larger than 1 inch while fine screens ranged as low as 0.25 inch. Over the last few decades, the sophistication of fine screens has improved and driven this range down. Currently, there are mechanical screens operating down to less than 1 mm in some municipal wastewater applications. It is generally recognized in today's market that coarse screens have openings down to 1 inch and fine screens below that. 6 mm or 0.25 inch is typical for fine screens. That "standard" continues to decrease with more sensitive downstream processes while screenings capture is increasing with improved designs and new opening types.

Figure 1:
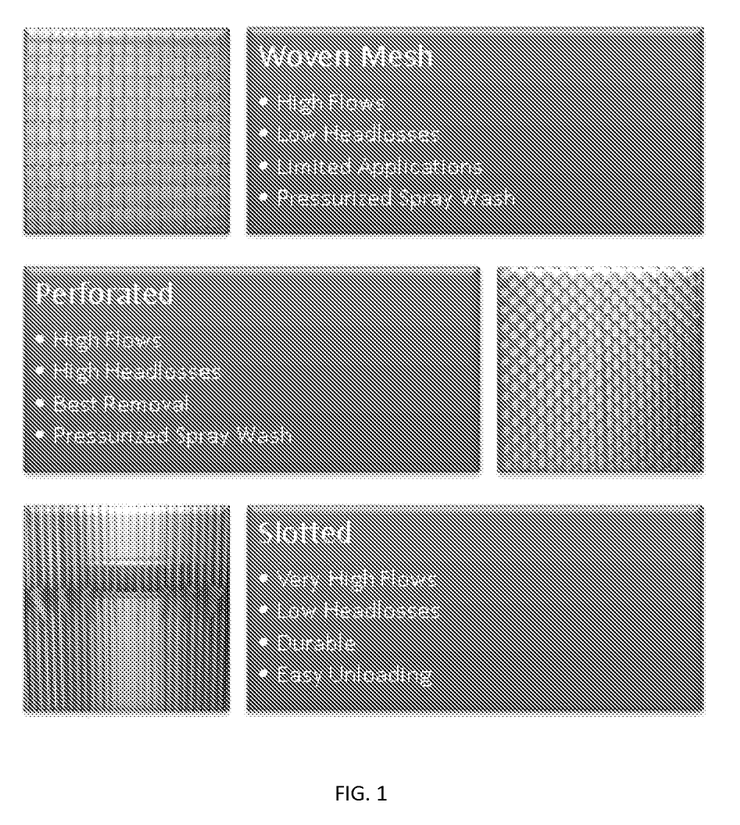
FIG. 1 is a diagram of screen types, according to an embodiment of the present invention.

Opening types of the screening equipment will now be discussed along with the illustrations of FIG. 1. There are three main types of mechanical screen grid openings: slotted, perforated and woven mesh. Each opening type has its advantages and limitations as well as suitable applications for use.

Slotted screen grids are typically manufactured of metal, found on coarser screens and can handle very large flows. They are commonly used with bar and continuous belt screens but are also used in other screen types. These screen types are used in water and wastewater treatment and while generally very durable and easy to unload they are less effective at removing smaller solids.

Perforated screen grids have circular holes machined or cut into plastic or metal panels and are found in finer screens with openings generally 0.25 inch or less. They are usually used in continuous belt screens in wastewater treatment applications. These openings capture the most screenings in wastewater applications but can have higher headlosses and require a spray wash to unload effectively.

Woven mesh grids are manufactured by framing wire mesh fabric with opening sizes generally less than 1 inch inside metal panels. They are also generally used in a continuous belt screen but are limited to water or treated wastewater applications as stringy materials are difficult to unload. Mesh opening screens can handle high volumes of water with low headlosses but are limited in solids they can remove and require a pressurized spray wash to unload captured screenings.

For wastewater treatment applications, slotted openings are commonly selected for coarser screens or where flow, channel, level, or lack of screening handling equipment limits higher screening capture. Perforated openings are increasing in popularity in wastewater applications because of their superior capture of solids but are sometimes not an option if an existing channel limits capacity or capture of organic material necessitates screening handling that is not desirable or affordable.

Figure 2:
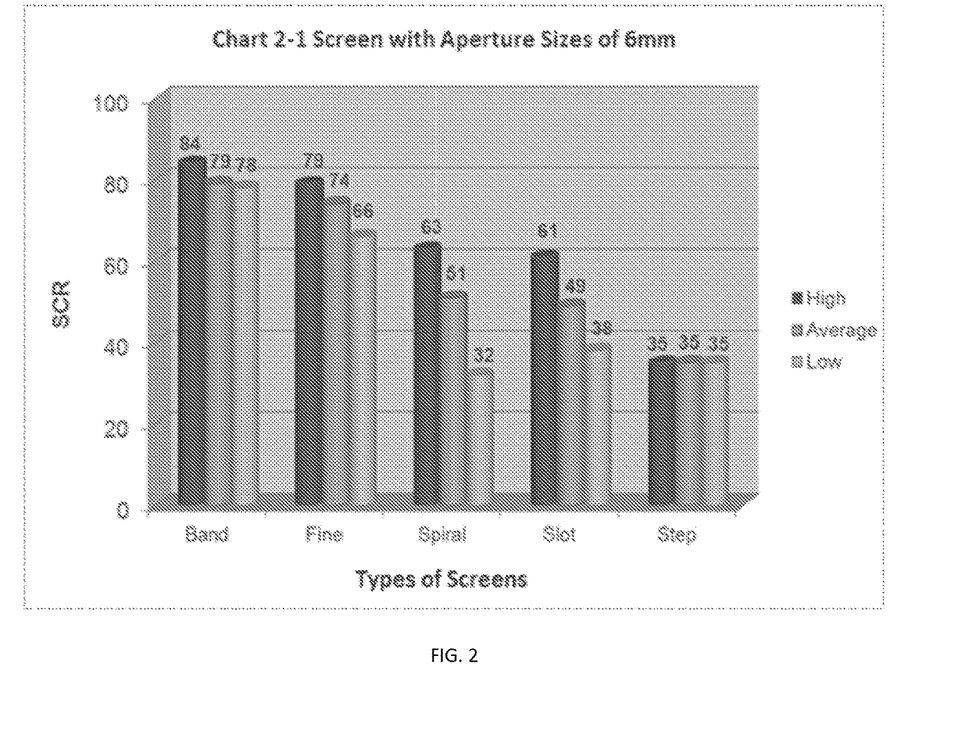
FIG. 2 is a chart illustrating flow rates for screen types, according to an embodiment of the present invention.

Selection of a screen type may be facilitated by considering one or more recognized evaluation of screen performance as Screenings Capture Ratio (SCR). A SCR is a measurement of the percentage of screenings a screen captures equal to or greater than its opening size. Thompson RPM, an independent testing facility based in the United Kingdom, and currently the only independent company actively engaged in testing screening equipment, recently published its findings on tests of SCR for more than 40 different screen designs. Chart 2-1 illustrated in FIG. 2 shows possible maximum, minimum, and average SCRs achieved for the different types of screening technologies tested at the facility. Their study tested 40+ screens of five different families (band, fine, screw, step, and slot) by eighteen different manufacturers with opening sizes from 1 mm to 7 mm and gives an accurate representation of the types of capture to be expected from screens of different families.

Screenings Capture Ratios may be considered when determining the proper screen for an application. Not all screens of the same opening size are created equal. As shown, even screens with the same opening size can have drastically different SCRs. In the 6 mm opening size the SCR was as low as 32% for a spiral style screen and as high as 84% for a center fed band style screen. A screen's orientation, unloading mechanism, sealing systems, and a number of other factors directly contribute to the amount of screenings a screen captures and retains.

This recent data regarding screen performance is useful in narrowing down a screen technology selection to a few screen types and opening sizes that are appropriate for a given application. From there, further evaluation should be made to ensure the proposed technology with the selected opening size is sized properly for the specific plant application.

Illustrative screen conditions and observations will now be discussed in the interest of clearly disclosing the present invention. The illustrative headworks at SCSD1 is an indoor facility that houses three screens. All of the screens at the headworks are multi-rake bar screens with a 0.25 inch opening. One of the screens is not functioning. The disassembled screw conveyor on the non-functioning screen is displayed in FIG. 3.

Figure 3:
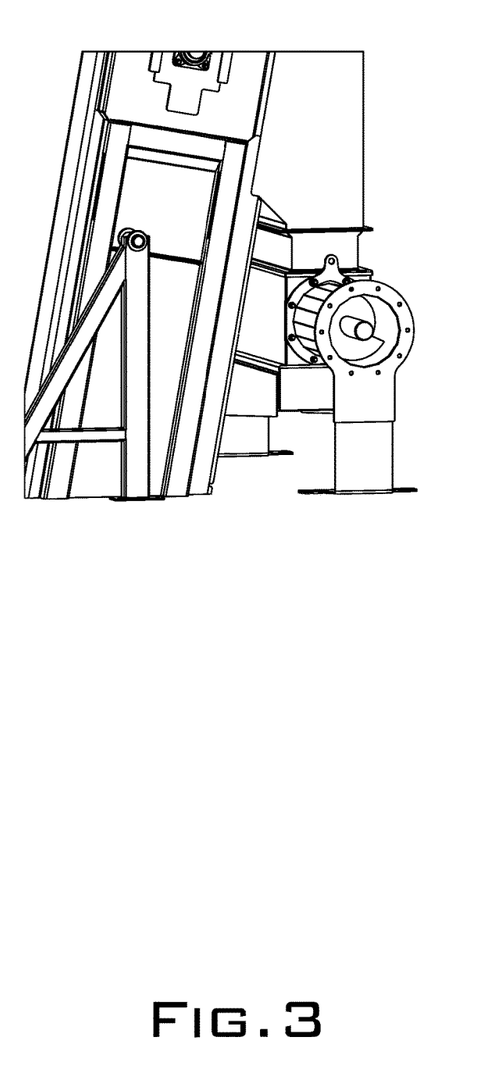
FIG. 3 is a photographic view of a filtration device usable with the system, according to an embodiment of the present invention.

The screen conveyor had to be disassembled because of the malfunctioning trough. The edge of the trough has broken and allows large solids to make it back to the system. The facility has rodents that may cause a sanitary issue if not addressed. The amount of screenings that are being removed from the channel on the bars is unsatisfactory. The solids that the system of the present invention is removing on the effluent side should be removed by the bars.

An example of the onsite screen sizing system will now be discussed. Throughout this disclosure, the onsite screen sizing system of the present invention may be alternatively labeled the "hydro-dyne onsite screen sizing," or "H.O.S.S.," system Skilled artisans should not view this alternative labeling to limit the present invention in any way.

The development of the H.O.S.S. system as a wastewater testing technology helps ensure the proper screen type has been selected for a unique application as well as correctly sizing the screen for the wastewater flow at a specific plant. The purpose of testing is to sample actual wastewater from the plant headworks and incorporate the findings in the design and proposal of screening equipment for that specific facility. The data may be compared to other tested facilities as well as interpreted through Hydro-Dyne's or another operator's experience in the performance of screening equipment to make proper recommendations. This can be an exclusive service offered by Hydro-Dyne Engineering to ensure that each proposed screen is designed specifically to cater to the needs of the plant in which it will operate.

The value of a screen specifically designed for the site constraints, downstream process and flow conditions to be experienced at a given plant cannot be understated. The detailed information collected pertaining to the consistency of the waste stream eliminates the guessing currently done by other manufacturers during screen design. Hydraulic calculations that are based on concrete data are accurate and unique for each plant. This ensures proposed screens are not over or under sized while still being designed to include appropriate safety factors. Benefits of a properly designed screen include: maximized SCR, which in turn leads to decreased maintenance across a plant, reduced screen maintenance, and increased screen life due to proper balance of idle versus run time, decreased capital costs attributed to oversized equipment and channels, prevents solids deposition prior to the screen and ensures that screenings handling units are designed to handle the solids expected to be captured by the screen.

Since it has been shown that not all screens of the same opening size perform equally, with SCRs between different style screens varying by as much as 50%, the H.O.S.S. system can also be used to measure the efficiency of an existing screen in service. By running trials both in front of and behind existing screens the H.O.S.S. system can be used to not only gauge the screens efficiency but also show the improvement in capture that should be expected for a screen of a different design and/or opening size.

The design of the onsite screen sizing system will now be discussed. The H.O.S.S. system is made up of various components specifically designed to pump wastewater from the waste stream through a simulated screening scenario and return it to the channel. The H.O.S.S. system may include intake piping, a flow meter, variable speed pump, multiple pressure sensors, the Sieve Assembly, discharge piping, and a programmable logic controller (PLC). The waste stream flow is pumped up through adjustable level intake piping, the flow meter, and sieve assembly before being piped back to the channel. The sieve assembly can accept slotted, perforated, and wire mesh sieve options simulating multiple opening shapes, sizes, and materials. The sieve assembly also allows two separate grids to be tested in series, simulating dual stage screening or stratifying screening size. Prior to each simulation, the parameters pertaining to each test (grid type, opening size, test duration, max differential, etc.) are programmed into the PLC via a touch screen panel.

Data collected by the sieve assembly and flow meter is then stored by the onboard PLC for interpretation by Hydro-Dyne Engineering or another authorized operator. Ultimately, the data collected may include increasing pressure losses across one or more sieves as they accumulate material larger than the openings, which can be charted relative to flow to deduce the concentration of solids above a certain size in the waste stream. The information can be used to design a screen of appropriate grid style, opening size and available open area to filter the waste stream.

In the interest of clarity, testing of the system and methods of the present invention will now be discussed without limitation. The testing described below was performed using a number of general procedures. Testing of the waste stream may be conducted over the course of a single day from early morning to late afternoon so that tests may be run under a range of flow conditions. Multiple day testing procedures may be used if seasonal flows impact solids loading. Test samples can be pumped from the influent channel just upstream of the existing screen. Samples may be taken from a range of depths in the channel to ensure tests are representative of solids concentrations across the channel. Ideally, test may be run for each opening size or type from the middle and bottom of the channel.

If the required opening size of a screen has not been determined, multiple opening sizes and grid types may be tested to determine the proper screen grid type for the application. Depending on the number of openings being tested, multiple days of testing may be required in order to obtain a sufficient amount of data pertaining to the opening sizes being evaluated for proper screen sizing.

In the performance evaluation of an existing screen, tests may be run at multiple levels on the influent and effluent sides with multiple opening sizes. Data is collected to determine solids presented to the screen of certain sizes and solids of the same size passing through the screen. In cases where there is no existing screen, wastewater samples are removed from proposed locations of future screening equipment or at the head of the plant. The removed wastewater may then be analyzed using the H.O.S.S. system to determine the solids capture for each tested opening size.

Prior to each individual trial, the PLC may set to log the details of the specific trial about to be run. Each trial may run until the sample screen panel for the desired opening size reaches a determinable blinding measurement. When the trial is complete, the sample screen panel is removed, visually examined for blow through and hairpinning, photographed and then cleaned for retesting. The test kit technician may examine the screenings and note any distinguishing characteristics of the screenings sample. More extensive data can also be attained by collecting captured screenings for further analysis.

Once a set of trials is complete, the data collected by the equipment is analyzed by Hydro-Dyne's or another authorized user's design engineers. This data may be compared to the findings recorded by previous tests run at other plants as well as industry standard design criteria for screening equipment. This analysis may then be used to draw up a custom designed screening unit that is sized specifically for that plant's channel, flows and expected solids quantities.

Figure 4:
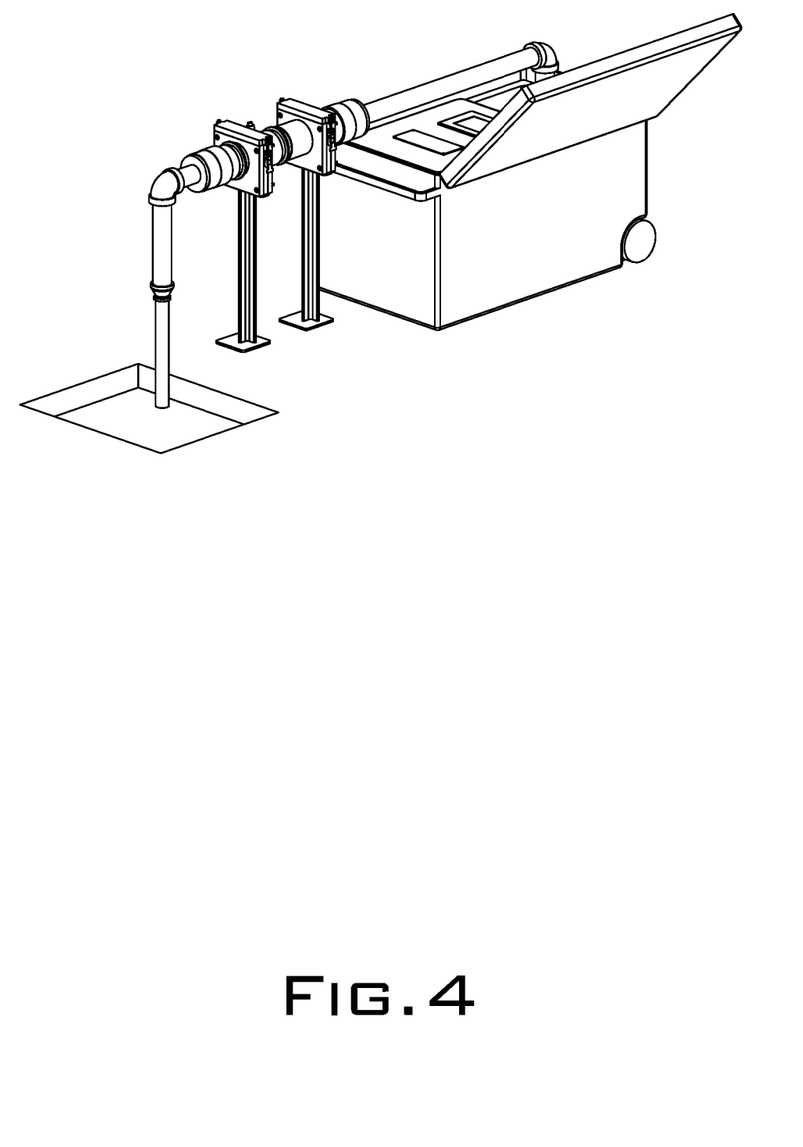
FIG. 4 is a perspective view of the test system in operation, according to an embodiment of the present invention.
Figure 5:
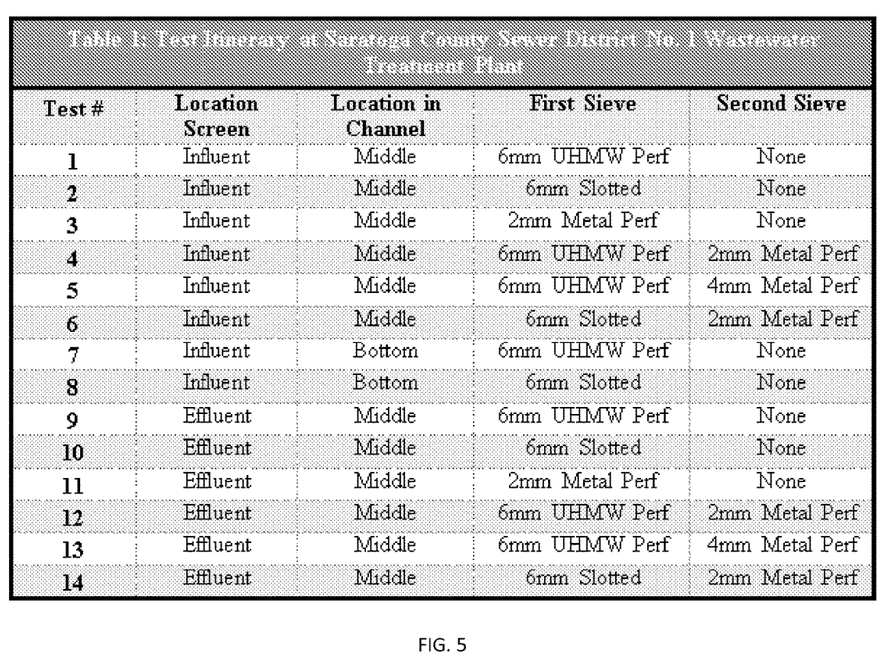
FIG. 5 is a table displaying an illustrative test itinerary, according to an embodiment of the present invention.

With reference to FIG. 4, plant specific testing will now be discussed. Those of skill in the art will appreciate that while the following example is provided by an instillation in a specific headworks and wastewater treatment plant, the installation and findings of the testing system may be applied to many other environments and installations. Therefore, skilled artisans should not view the following illustrative testing installation to limit the present invention in any way. The system of FIG. 4 provides a H.O.S.S. system setup inside a headworks at Saratoga County Sewer District No. 1 Wastewater Treatment plant. Skilled artisans will not view this testing configuration as limiting in any way. A list of illustrative tests executed at Saratoga County Sewer District No. 1 Wastewater Treatment Plant is provided in FIG. 5.

Figure 6:
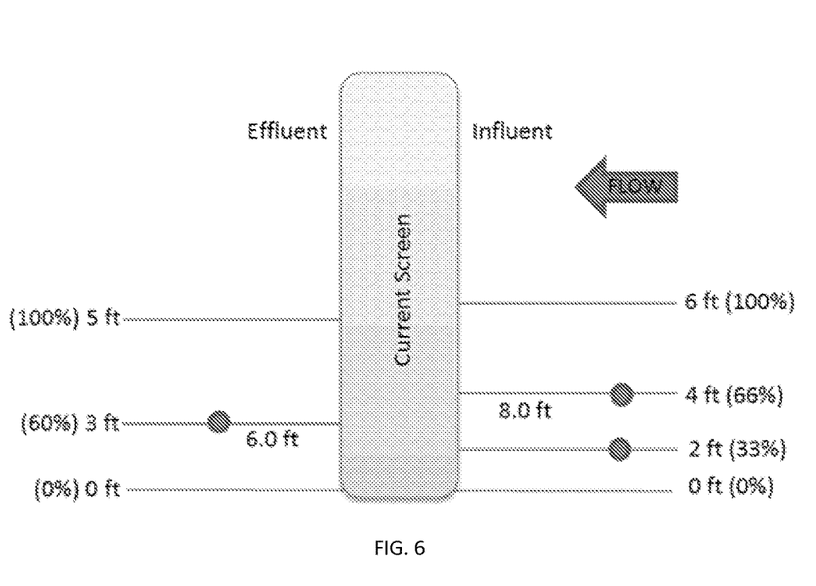
FIGS. 6-7 are block diagrams of illustrative test procedures, according to an embodiment of the present invention.
Figure 7:
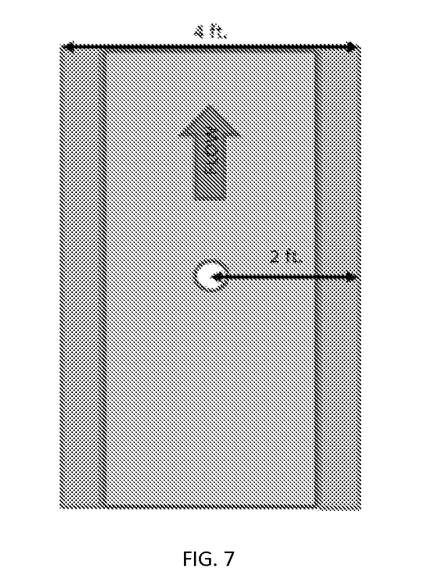
Figure 8:
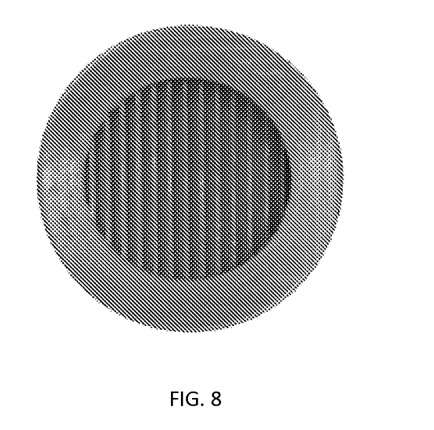
FIG. 8 is a diagram of a slotted screen type, according to an embodiment of the present invention.
Figure 9:
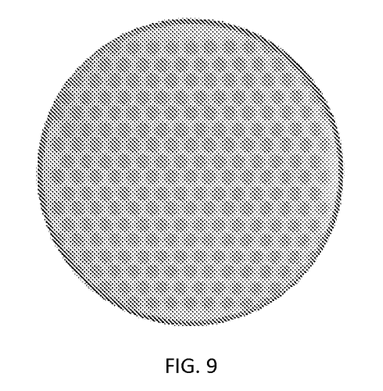
FIG. 9 is a diagram of a first perforated screen type, according to an embodiment of the present invention.
Figure 10:
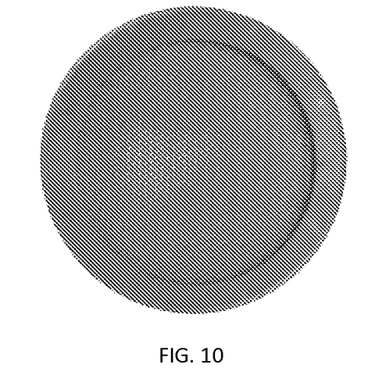
FIG. 10 is a diagram of a second perforated screen type, according to an embodiment of the present invention.

Screen types were chosen based on hydraulic sizing. The tests were performed in the channel at the headworks. FIG. 6 provides a diagram representing where the tests were executed in relation to the screen and bottom of the channel. The approximate influent depth of the wastewater was 6 ft. Samples were removed 8 ft. from the front of the screen at depths of approximately 4 ft. and 2 ft. above the base of the channel. The tests performed on the effluent side of the screens were 6 ft. away from the screen because it allowed for the best access to the channel. The approximate effluent depth was 5 ft. and the samples were taken approximately 3 ft. from the base of the channel. FIG. 7 shows an illustrative placement of the pipe used to extract wastewater from the channel.

Figure 11:
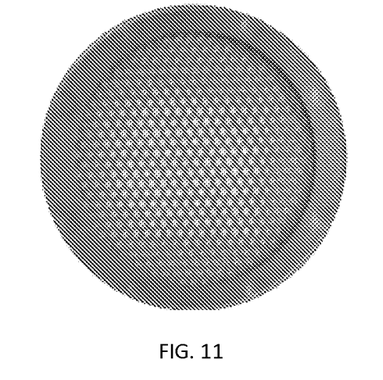
FIG. 11 is a diagram of a third perforated screen type, according to an embodiment of the present invention.
Figure 12:
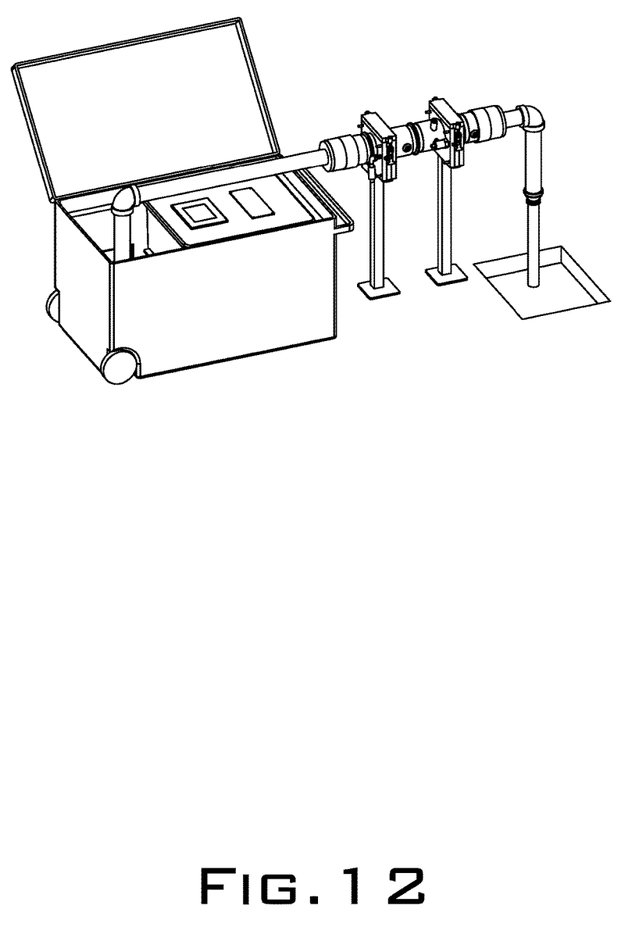
FIGS. 12-16 are photographic images illustrating features of various embodiments of the present invention.
Figure 13:
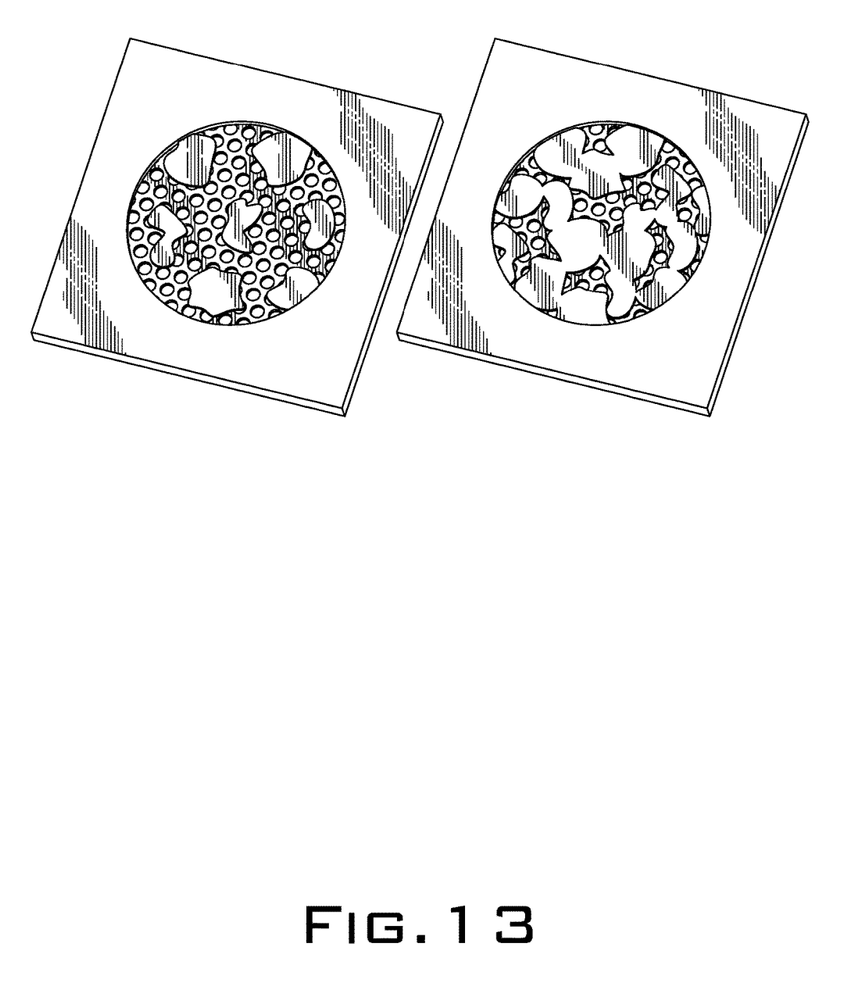

The pipe used to extract the wastewater to pass through the test kit was located in the center of the channel because the velocity of the flow is the fastest. Fast velocity is important because it allows the H.O.S.S. system to pump solids that have not settled out on the slower edges of the channel. Settling out can be caused by the velocity of the flow, the particle diameter, the density of the particle, and the shape of the screening. Below in FIGS. 8-11 are the sieves used in the test kit to represent the 6 mm slotted (FIG. 8), 6 mm UHMW perforated panel (FIG. 9), 2 mm metal perforated panel (FIG. 10), and 4 mm metal perforated panel (FIG. 11).

Figure 14:
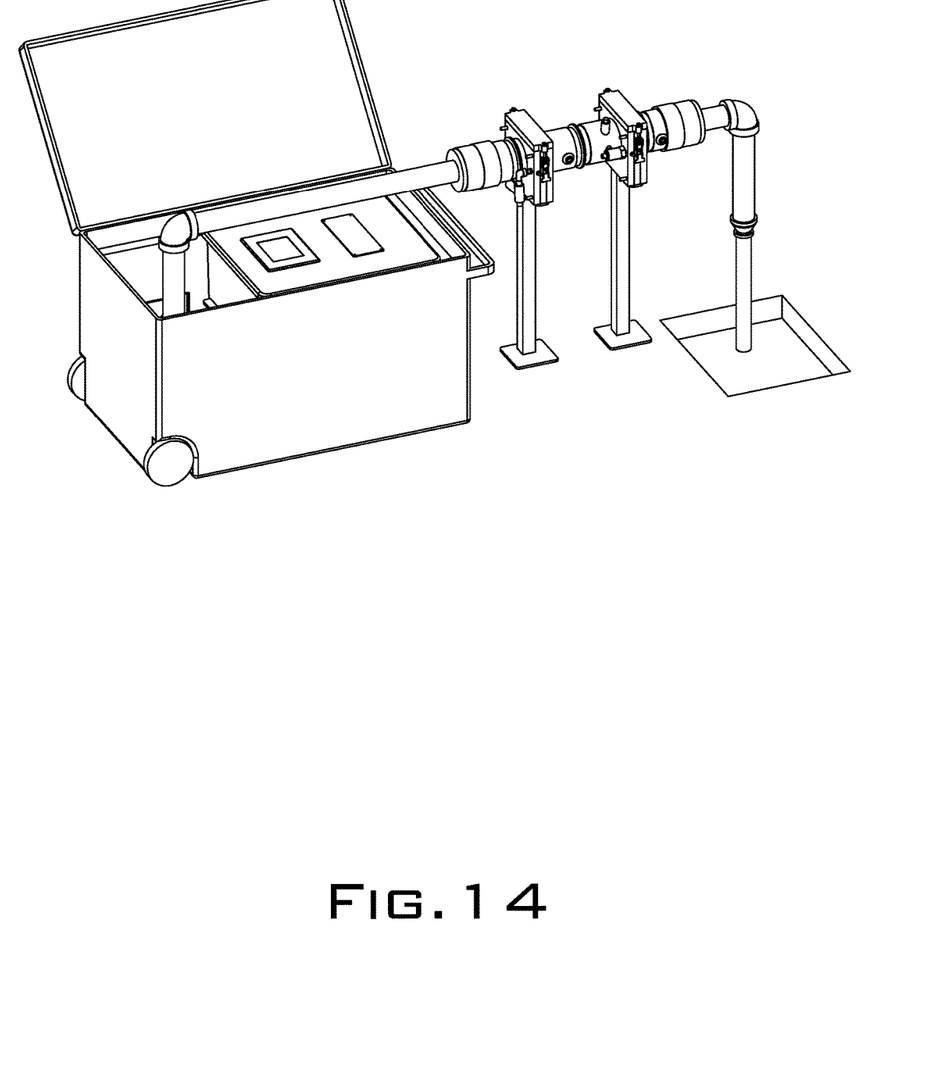
Figure 15:
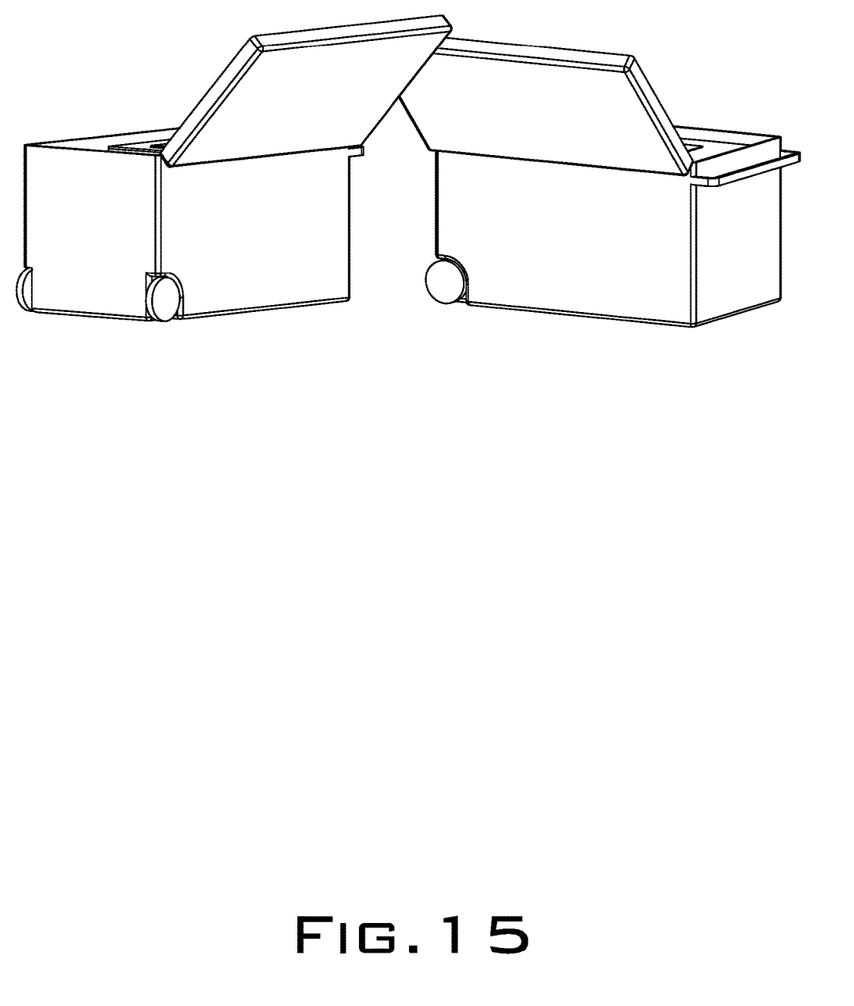
Figure 16:
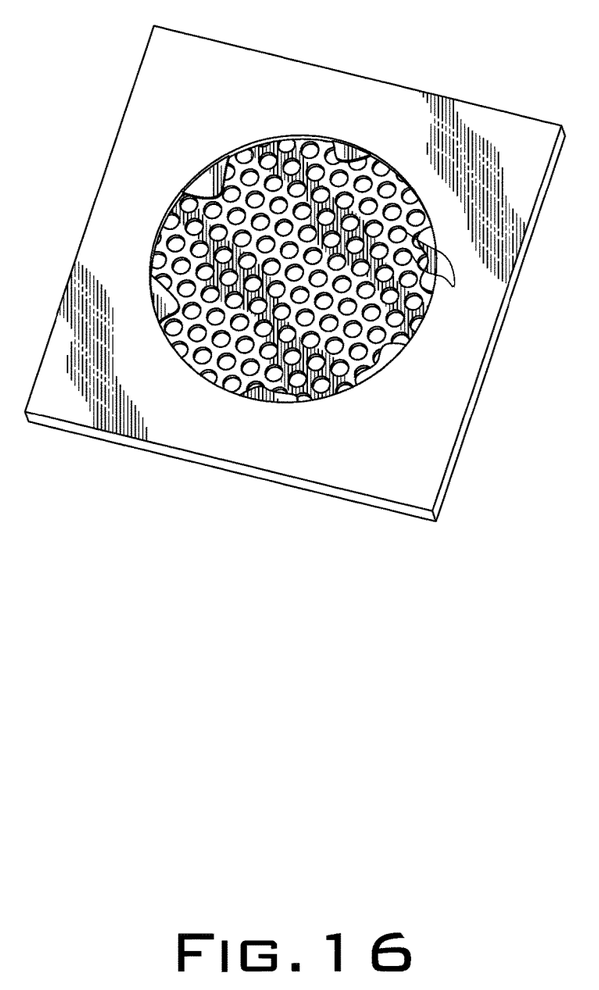

FIGS. 12-16 are photographic images illustrating other features, according to one or more embodiments of the present invention. In particular, FIG. 14 illustrates an embodiment of the system that may include an electric motor; storage container; control panel with programmable logic control, variable speed pump drive, and data recorder; intake for pump; housing for interchangeable sieves for testing flow through different size and shape openings; and output for tested flow returning to the plant.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for evaluating a waste stream, comprising:
a wastewater treatment system comprising a channel through which wastewater flows and a screen installed in the channel through which the wastewater passes;
a screen sizing system comprising:
at least one pipe to extract wastewater from the channel for testing, wherein the at least one pipe is installable in the channel in front of the screen to conduct testing of influent wastewater flowing toward the screen; and wherein the at least one pipe is installable in the channel downstream from the screen to conduct testing of effluent wastewater that has already passed through the screen;

a pump for pumping water from the channel through the pipe;

a testing module for testing a flow and downstream process of the wastewater treatment system;

an analytic module for analyzing results of the testing;

a housing for receiving at least two interchangeable sieves to test flow of the wastewater through the at least two interchangeable sieves to determine selection of the screen or a different screen that is optimized for use by the wastewater system to capture solids in the wastewater; and a screen to be selected by applying the results;

wherein at least one characteristic of the waste stream is tested.

2. The system of claim 1, wherein the at least one characteristic comprises a screen type and an opening size.

3. A method for evaluating a waste stream, comprising the steps of:

(a) testing a flow and downstream process of a wastewater treatment system comprising a channel through which wastewater flows and a screen installed in the channel through which the wastewater passes, wherein the testing is conducted using a screen sizing system comprising:

at least one pipe to extract wastewater from the channel for testing, wherein the at least one pipe is installable in the channel in front of the screen to conduct testing of influent wastewater flowing toward the screen; and wherein the at least one pipe is installable in the channel downstream from the screen to conduct testing of effluent wastewater that has already passed through the screen;

a pump for pumping water from the channel through the pipe;

a testing module for testing a flow and downstream process of the wastewater treatment system;

an analytic module for analyzing results of the testing;

a housing for receiving at least two interchangeable sieves to test flow of the wastewater through the at least two interchangeable sieves to determine selection of the screen or a different screen that is optimized for use by the wastewater system to capture solids in the wastewater;

(b) analyzing results of the testing; and (c) applying the results to select a screen;

wherein at least one characteristic of the waste stream is tested.

4. The method of claim 3, wherein selecting the screen in step (c) of the method further comprises the steps of:

determining a screen type;

determining an opening size; and selecting the screen with the screen type and the opening size to optimize flow characteristics.

* * * * *